(12) United States Patent
Brinkman (10) Patent No.: US 8,275,465 B2
(45) Date of Patent: Sep. 25, 2012

(54) STIMULATION LEAD FOR APPLICATION OF ELECTRICAL PULSES TO TISSUE OF A PATIENT AND METHOD FOR FABRICATING A STIMULATION LEAD

(75) Inventor: Cory Brinkman, Celina, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 119 days.

(21) Appl. No.: 12/980,862

(22) Filed: Dec. 29, 2010

(65) Prior Publication Data

US 2011/0160815 A1 Jun. 30, 2011

Related U.S. Application Data

(60) Provisional application No. 61/290,656, filed on Dec. 29, 2009.

(51) Int. Cl.
*A61N 1/00* (2006.01)
(52) U.S. Cl. .................................................. 607/115
(58) Field of Classification Search .................... 607/115
See application file for complete search history.

(56) References Cited

U.S. PATENT DOCUMENTS 3,995,623 A * 12/1976 Blake et al. ................. 600/381
5,458,629 A 10/1995 Baudino et al.

* cited by examiner

*Primary Examiner* — George Manuel
*Assistant Examiner* — Robert N Wieland
(74) *Attorney, Agent, or Firm* — Craig Hoersten; Christopher S. L. Crawford; Peter R. Lando (57) ABSTRACT

A method of fabricating a stimulation lead by supplying a lead body with a plurality wire conductors extending the length of the lead body and being within insulative material therein; providing a plurality of terminals and electrodes on the ends of the lead body, wherein the plurality of terminals and electrodes are electrically coupled, wherein the providing comprises: (i) positioning a conductive band about the lead body that is adapted to be clasped about the lead body; (ii) positioning a conductor wire between an exterior surface of the first end and an interior surface of the second end of the conductive band; (iii) closing overlapping ends of the conductive band about the conductor wire; and (iv) welding the ends to seal the conductive band about the lead body.

19 Claims, 5 Drawing Sheets

STIMULATION LEAD FOR APPLICATION OF ELECTRICAL PULSES TO TISSUE OF A PATIENT AND METHOD FOR FABRICATING A STIMULATION LEAD

CROSS-REFERENCE TO RELATED APPLICATIONS

This application claims the benefit of U.S. Provisional Application No. 61/290,656, filed Dec. 29, 2009, which is incorporated herein by reference.

TECHNICAL HELD

This application is generally related to a stimulation lead for application of electrical pulses to tissue of a patient and method for fabricating a stimulation lead.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. Applying electrical energy to the spinal cord associated with regions of the body afflicted with chronic pain can induce "paresthesia" (a subjective sensation of numbness or tingling) in the afflicted bodily regions which can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator.

Each stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted at the location adjacent or within the tissue to be electrically stimulated. The proximal end of the stimulation lead is connected to the header to the pulse generator or to an intermediate "extension" lead.

The manufacture of stimulation leads is a relatively complex process. Some manufacturing techniques involve wrapping conductor wires with insulative coatings about a mandrel in a helical manner to form a lead body. An example of a system adapted to perform such winding is shown in U.S. Pat. No. 7,287,366, entitled "Method for producing a multielectrode lead," which is incorporated herein by reference. Upon fabrication of a lead body electrodes and terminals are provided to the lead body. A variety of techniques exist for electrode and terminal fabrication. Some known techniques involve employing a "blind weld" to electrically couple a respective electrode to a wire of the lead body.

SUMMARY

In one embodiment, a method of fabricating a stimulation lead for applying electrical pulses to tissue of a patient, comprises: supplying a lead body, wherein the lead body comprises a plurality of wire conductors extending from a proximal end of the lead body to a distal end of the lead body, and the plurality of conductor wires are disposed within insulative material of the lead body; and providing a plurality of terminals and electrodes on the proximal end and the distal end of the lead body respectively, wherein the plurality of terminals and electrodes are electrically coupled through the plurality of wire conductors; wherein the providing comprises: (i) positioning a conductive band about the lead body, wherein the conductive band comprises a first end and a second end and the first end and second end are adapted to be clasped together; (ii) positioning a conductor wire between an exterior surface of the first end and an interior surface of second end of the conductive band; (iii) closing the first end and second end of the conductive band about the conductor wire wherein the first end and second end are disposed in an overlapping arrangement; and (iv) welding the first end and second end to seal the conductive band about the lead body.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
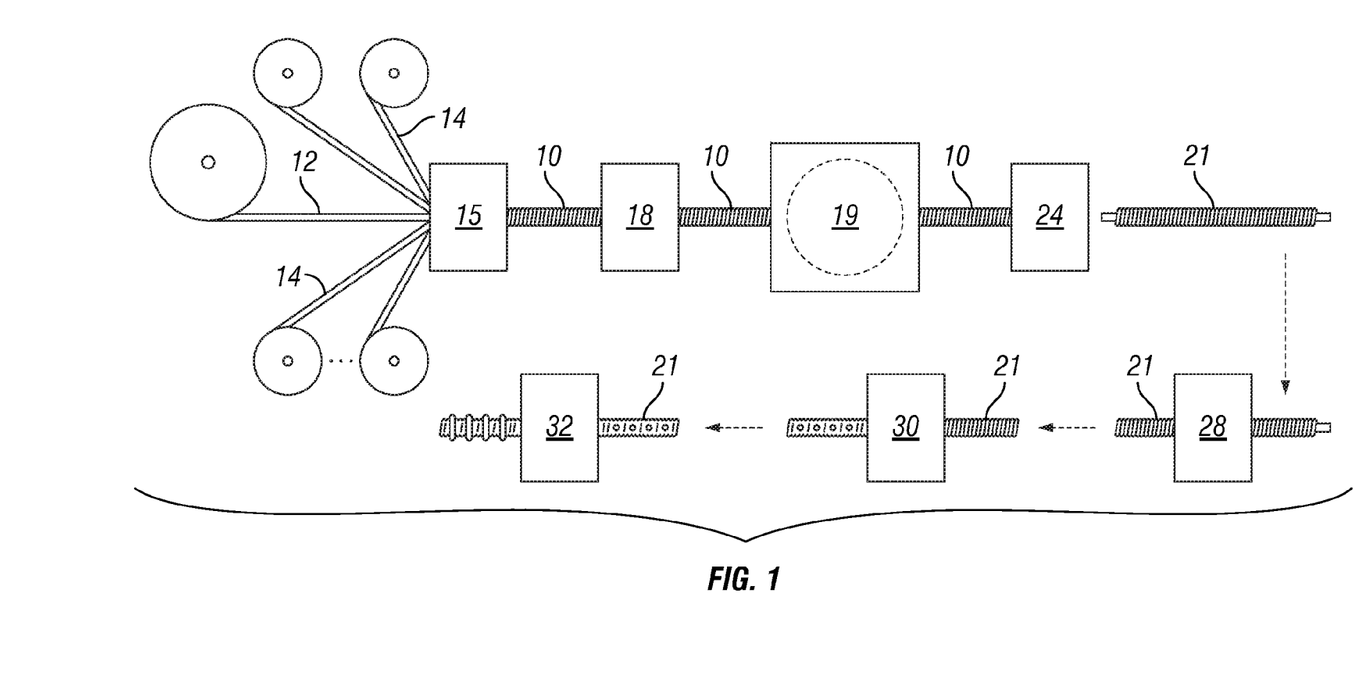
FIG. 1 depicts a process for fabricating a lead body according to one representative embodiment.
Figure 2:
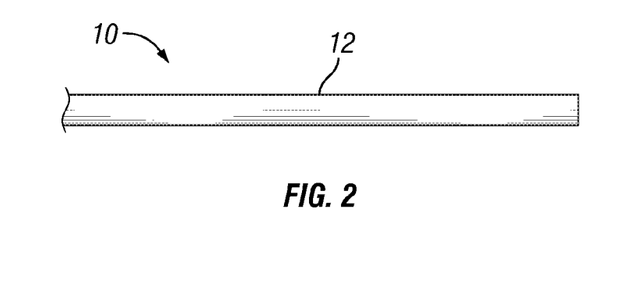
FIG. 2 depicts a mandrel for use in fabricating a lead body.

In one embodiment, a process for fabricating lead body material for stimulation leads begins with a continuous core material 10 shown in FIG. 1. In one embodiment, the core material 10 is a polytetrafluoroethylene (PTFE) coated stainless steel mandrel wire 12 (shown in FIG. 2), although additional insulative layers may also be provided according to other embodiments. Referring again to FIG. 1, the core material 10 is then helically wrapped with a set of insulated wires 14 at a wire wrapping system 15. Systems for helically winding wires for fabrication of a lead body are disclosed in U.S. Provisional Application Ser. No. 61/247,264, entitled "System and method for fabricating a stimulation lead," and U.S. Pat. No. 7,287,366, entitled "Method for producing a multi-electrode lead," which are incorporated herein by reference.

Each of the wires 14 may include one or more layers of insulation. In one embodiment, each wire 14 comprises an inner thin layer of perfluoroalkoxy (PFA) and outer thicker layer of a thermoplastic silicone polycarbonate urethane (e.g., CARBOSIL™). While eight insulated wires are used in one embodiment, those skilled in the art will recognize that any suitable number of wires may be wrapped onto mandrel 12 according to other embodiments. In other embodiments, additional layers of wires 14 may be wound over the initial layer(s) of wires.

Figure 3:
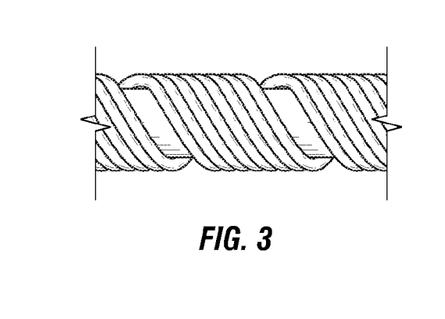
FIG. 3 depicts a segment of a lead body fabricated according to one representative embodiment.

In one preferred embodiment, wires 14 are wrapped about core material 10 in an axially repeating pattern of groups 301 of closely spaced wires with each group 301 separated by distance 302 that is larger than the spacing between adjacent wires within each group (FIG. 3). The distance between groups in FIG. 3 is by way of example and any suitable distance may be employed according to some embodiments.

Referring again to FIG. 1, core material 10, now comprising mandrel 12 and helically wrapped insulated wires 14 may now be spooled and later unspooled (not shown) or fed directly to the next step in the process. In the next step, core material 10 may be selectively and repeatedly heated in a reflow oven 18. The wires 14 are heated to a temperature that causes the insulation of insulated wires 14 to approach or achieve a phase change, thereby becoming soft and adherent and ultimately fusing together, by heating, melting and re-solidifying after removal from reflow oven 18.

At this point, the core material 10, now comprising mandrel 12 having insulated wires 14 at least partially fused about it, may now be spooled (step 19) onto a spool and stored for later work. Alternatively, step 19 is not performed and core material 10 proceeds directly to the remaining steps. Continuous core material 10 is cut (step 24) into individual lead bodies 21. Each individual lead body 21 may have a length of from about 10 cm (4 in) to about 150 cm (60 in).

After the lead bodies 21 have been cut to length, mandrel 12 is removed in a mandrel removal step 28. This task may be facilitated by a coating of mandrel 12 that will ease removal, such as a PTFE coating. The mandrel removal step 28 may be a simple hand operation by a human worker.

Next, in an electrode creation step 30, electrodes are provided on the distal end of the lead body. In step 32, terminals are provided on the proximal end of the lead body. Electrode and terminal fabrication are further discussed below.

Figure 4:
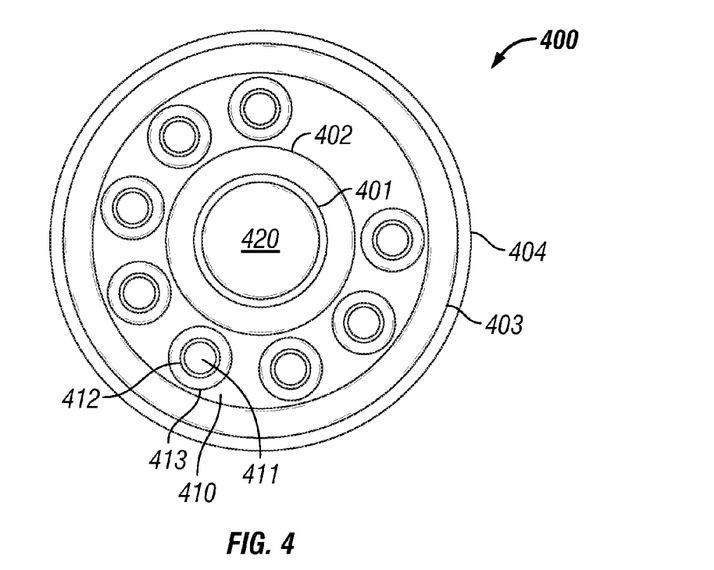
FIG. 4 depicts a cross-sectional view of a lead body assembly according to one representative embodiment.

FIG. 4 depicts a cross-sectional view of lead body assembly 400 according to one representative embodiment. Lead body assembly 400 comprises stainless steel mandrel 420 which is coated with layer 401 of PTFE. Inner layer 402 of CARBOSIL™ is extruded or otherwise provided over the inner layer of PTFE. The mandrel 420 with layers 401 and 402 is utilized as core material 10 in wire wrapping system 15. Each wire 410 (only one wire is annotated for the sake of clarity) is preferably stranded wire coated with a thin layer of PFA and a thicker layer of CARBOSIL™. Wire wrapping system 15 wraps a plurality of wires 410 about mandrel 420, layer 401, and layer 402 in the manner discussed above. An outer layer 403 of CARBOSIL™ is also provided. Shrink wrap tubing 404 is then provided on the exterior of the assembly.

Figure 5:
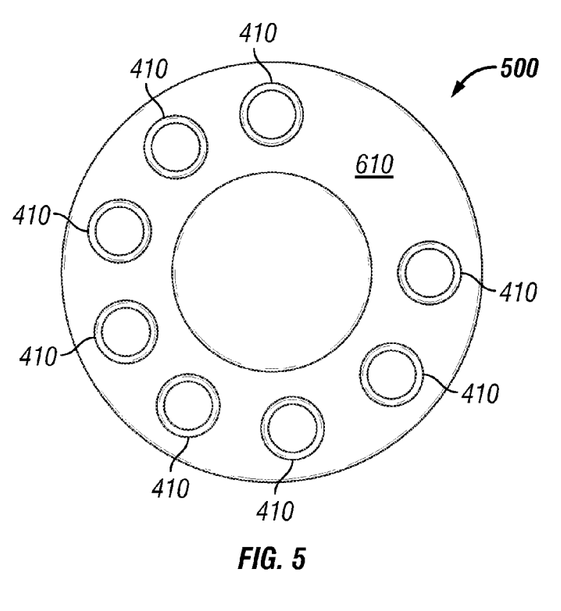
FIG. 5 depicts a lead body fabricated according to one representative embodiment.

Lead body 400 is cut to length and lead body assembly 400 is subjected to heating above the melting point of the thermoplastic material. The heat and pressure (e.g., from heat shrinkable tubing) causes the thermoplastic insulative material (e.g., the CARBOSIL™ material) to flow. After the thermoplastic material is cooled, the thermoplastic material re-solidifies into a lead body 500 of fused insulative material enclosing the respective conductors 410. Also, as shown in FIG. 16, gap 610 is provided within lead body 500 where no conductors are located within gap 610. That is, gap 610 is entirely filled with insulative material.

In one embodiment, the lead body is fabricated so that the lead body is capable of elastic elongation under relatively low stretching forces. Also, after removal of the stretching force, the lead body is capable of resuming its original length and profile. For example, in one embodiment, relatively low durometer, elastic polymer material is used for the material of the lead body. The combination of the selection of the materials, the helically wrapping of the wires, and the repeating groups of wires with separating gaps enables the stretching according to the relatively low stretching forces. For example, the lead body may stretch 10%, 20%, 25%, 35%, or even up to 50% at forces of about 0.5, 1.0, and/or 2.0 pounds of stretching force. For additional description of a lead body capable of elastic elongation, reference is made to U.S. Patent Publication No. 2007/0282411, entitled "COMPLIANT ELECTRICAL STIMULATION LEADS AND METHODS OF FABRICATION," which is incorporated herein by reference. Although some specific lead body fabrication techniques are discussed herein, any suitable processes may be employed for lead fabrication. Alternative example lead fabrication processes are discussed in U.S. Pat. Nos. 5,555,618 and 6,216,045, which are incorporated herein by reference.

Lead body 500 is then cut into appropriate lengths and electrodes and terminals are provided.

Figure 6:
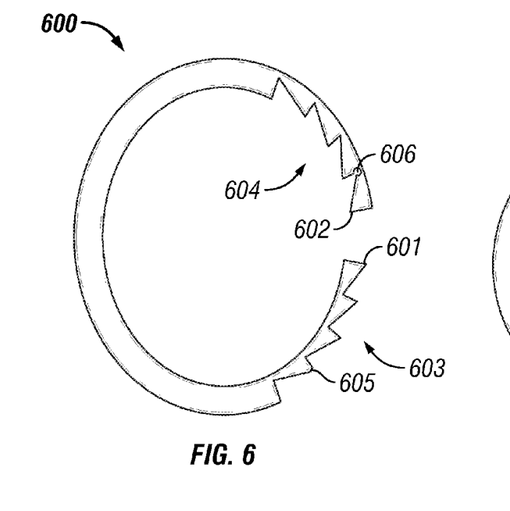
FIG. 6 depicts a cross-sectional view of a conductive band in an open configuration according to one representative embodiment.
Figure 7:
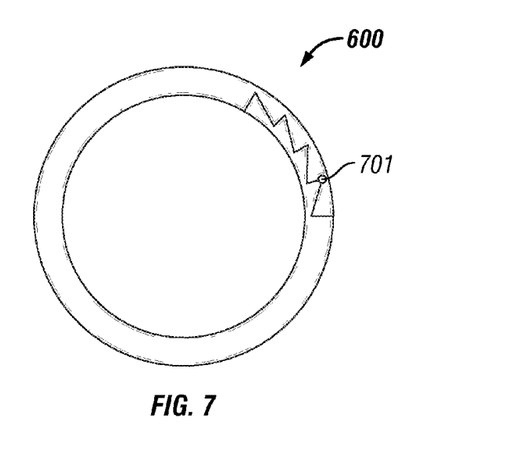
FIG. 7 depicts a cross-sectional view of a conductive band in a dosed configuration according to one representative embodiment.

FIG. 6 depicts a cross-sectional view of conductive band 600 according to one representative embodiments. Conductive band 600 may be employed to provide the electrodes and/or terminals of a stimulation lead. Conductive band 600 may be fabricated using any suitable conductive material. In one specific embodiment, conductive band 600 is fabricated using a platinum iridium ahoy. Conductive ring is not a single continuously connected ring of material. Instead, band 600 comprises first end 601 and second end 602. First end 601 and second end 602 are moveable. Conductive band 600 may be placed in an open position as shown in FIG. 6. Conductive bands 600 is also adapted to be placed in a dosed position as shown in FIG. 7 with first end 601 and second end 602 disposed in an overlapping arrangement.

Referring to FIG. 6, conductive band 600 comprises opposing surface features 603 and 604. Surface feature 603 is disposed on an "exterior" side of end 601 and surface feature 604 is disposed on an "interior" side of end 602. Surface features 603 and 604 may be formed using suitable miffing or laser etching techniques. Surface features 603 and 604 are adapted to interconnect or mate with each other. In one embodiment, surface features 603 and 604 comprise a sawtooth pattern. Also, in one embodiment, band 600 is implemented to possess a spring-characteristic which provides a biasing force to press surface features 603 and 604 against each other when band 600 is placed in the closed position.

Figure 8:
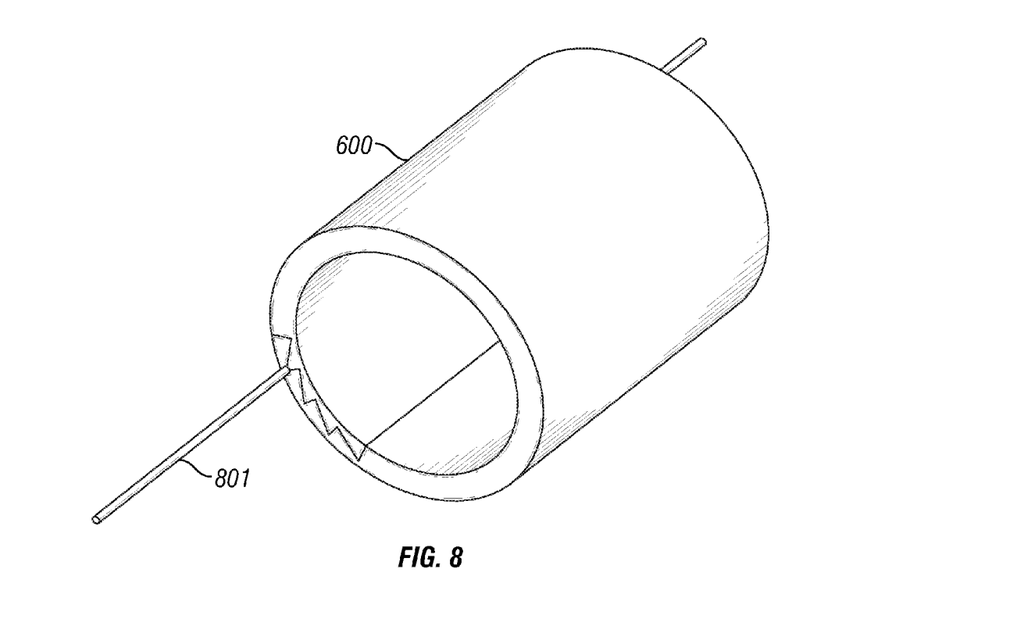
FIG. 8 depicts an isometric view of a conductive band with a conductor placed within the conductive band according to one representative embodiment.

Surface features 603 and 604 optionally include sub-features 605 and 606, respectively. Sub-features 605 and 606 are adapted to clamp about a conductive wire when band 600 is placed in the closed position. FIG. 7 depicts conductive band 600 in the closed position. As shown in FIG. 7, conductive band 600 includes recess 701 (formed by sub-features 605 and 606). Recess 701 is adapted to the size of a suitable conductive wire for electrical connection with conductive band 600 when conductive band 600 is integrated with the lead body. FIG. 8 depicts an isometric view of conductive band 600 in the closed position with conductive wire 801 crimped within recess 701. After wire 801 is placed within conductive band 600 is this manner, laser or other suitable welding is preferably applied to permanently seal conductive band 600.

Figure 9:
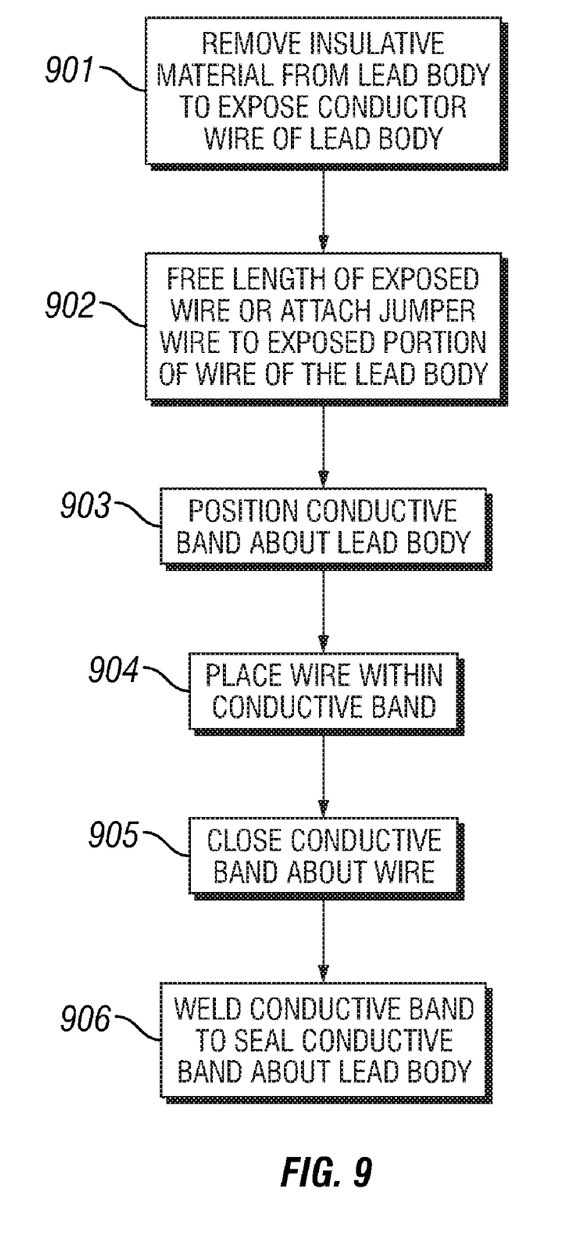
FIG. 9 depicts a process for providing an electrode or a terminal on a lead body during fabrication of a stimulation lead according to one representative embodiment.

FIG. 9 depicts a process for providing an individual terminal or electrode on a lead body of a stimulation lead under fabrication. The process of FIG. 9 may be repeated for each of the electrodes and/or terminals to be provided on the end-product stimulation lead.

In 901, insulative material is removed from the lead body to expose a conductor wire of lead body. The insulative material may be removed using any suitable technique. Manual operations may be employed. In another embodiment, a suitable laser may be employed to ablate insulative material from the lead body.

In 902, a length of the exposed wire is freed from the lead body. Alternatively, a jumper wire may be attached to the exposed portion of the conductor wire of the lead body (see e.g., U.S. Pat. No. 6,952,616, entitled "Medical lead and method for electrode attachment," which is incorporated herein by reference).

In 903, conductive band 600 is provided about the lead body adjacent to the exposed wire of the lead body.

In 904, the exposed wire or the jumper wire is placed within conductive band 600. Conductive band 600 is then closed about the wire (905) and around the lead body. In some embodiments, the wire is positioned within an interior aperture or recess 701 of conductive band 600 when the conductive band is closed. Conductive band 600 is subjected to laser welding or other suitable welding to permanently seal the conductive band about the lead body (906).

It is believed that the electrode fabrication according to some embodiments may provide one or more advantageous. For example, a "blind" weld is not required for some embodiments. Also, the welding technique of some embodiments is less technique dependent and may result in greater manufacturing yields. Moreover, it is believed that the mechanical characteristics involved with the conductor wire and the conductive band for some embodiments may be more robust than other known attachment techniques. Also, since crimping is not necessarily employed, less scrap material may be used for some embodiments.

Figure 10:
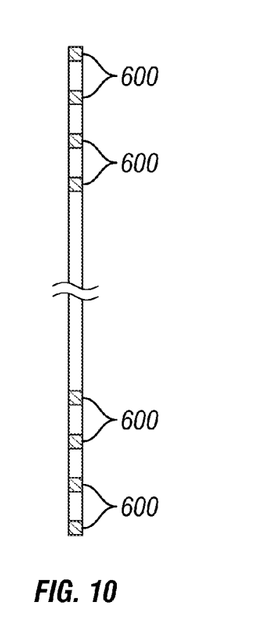
FIG. 10 depicts a stimulation lead according to one representative embodiment.

FIG. 10 depicts percutaneous lead 1000 fabricated according to some embodiments. Lead 1000 comprises a plurality of electrodes and terminals fabricated using conductive bands 600 according to some representative embodiments. Although lead 1000 is shown to be fabricated as a "percutaneous lead," other lead designs may also be employed such as paddle-style leads where only the terminals are fabricated using conductive bands 600. Also, not all of the electrodes of a stimulation lead need involve the use of band 600. For example, a conventional "tip" electrode design could be employed for the most distal electrode of lead 1000 if desired for a particular medical therapy. Further, although some embodiments have discussed fabrication of neurostimulation leads, other medical leads may be fabricated according to other embodiments, such as cardiac leads, mapping leads, ablation leads, etc.

Figure 11:
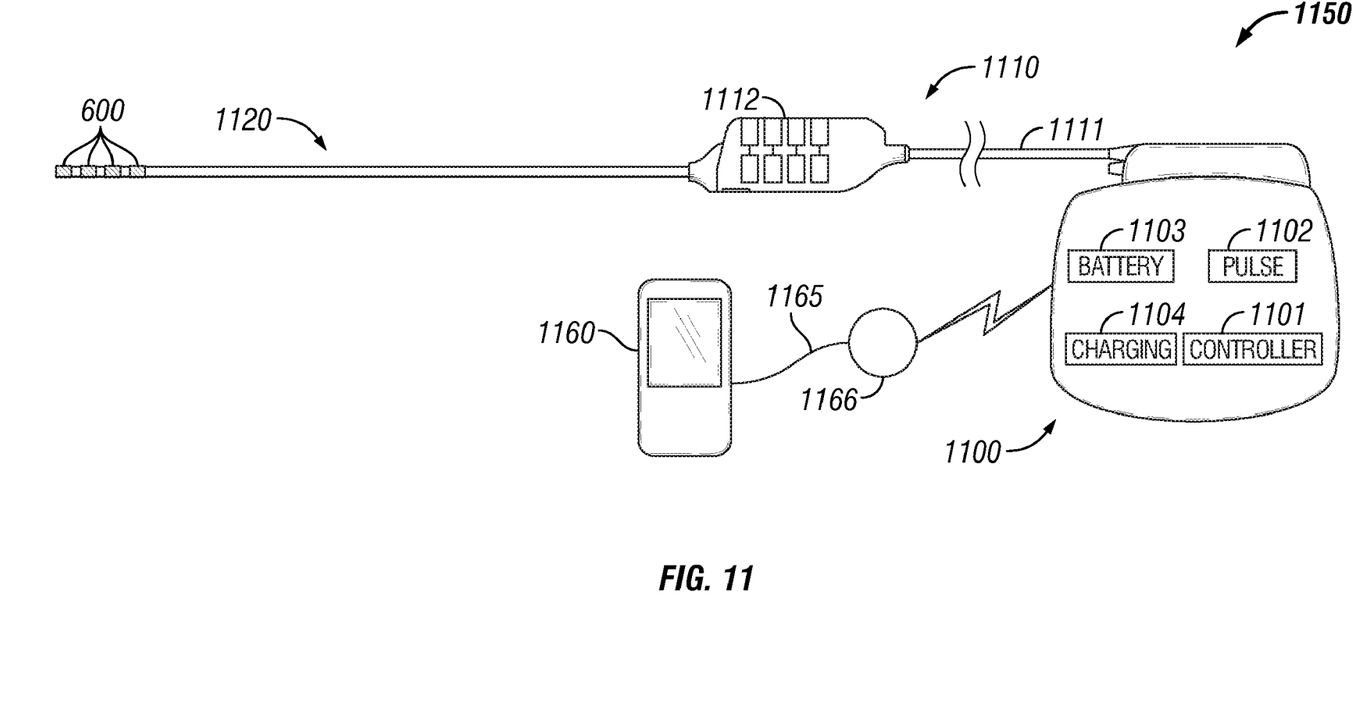
FIG. 11 depicts a stimulation system according to one representative embodiment.

FIG. 11 depicts stimulation system 1150 that generates electrical pulses for application to tissue of a patient according to one embodiment. In one embodiment, system 1150 is adapted to generate electrical pulses and deliver the pulses to tissue of the patient. For example, system 1150 may be adapted to stimulation spinal cord tissue, peripheral nerve tissue, deep brain tissue, cortical tissue, cardiac tissue, digestive tissue, pelvic floor tissue, or any other suitable tissue within a patient's body.

System 1150 includes implantable pulse generator 1100 that is adapted to generate electrical pulses for application to tissue of a patient. Implantable pulse generator 1100 typically comprises a metallic housing that encloses pulse generating circuitry 1102, controller 1101, charging coil (not shown), battery 1103, far-field and/or near field communication circuitry (not shown), battery charging circuitry 1104, etc. of the device. Although an implantable pulse generator is shown for the embodiment of FIG. 11, an external pulse generator (e.g., a "trial" stimulator) may alternatively be employed. The controller 1101 typically includes a microcontroller or other suitable processor for controlling the various other components of the device. Software code is typically stored in memory of the pulse generator 1100 for execution by the microcontroller or processor to control the various components of the device.

A processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 1100. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation system 1150 further comprises one or more stimulation leads 1120. Stimulation lead 1120 comprises a lead body of insulative material about a plurality of conductors that extend from a proximal end of lead 1120 to its distal end. The conductors electrically couple a plurality of electrodes 600 to a plurality of terminals (not shown) of lead 1120. The terminals are adapted to receive electrical pulses and the electrodes 600 are adapted to apply stimulation pulses to tissue of the patient. Also, sensing of physiological signals may occur through electrodes 600, the conductors, and the terminals. Additionally or alternatively, various sensors (not shown) may be located near the distal end of stimulation lead 1120 and electrically coupled to terminals through conductors within the lead body 1111.

Stimulation system 1150 optionally comprises extension lead 1110. Extension lead 1110 is adapted to connect between pulse generator 1100 and stimulation lead 1120. That is, electrical pulses are generated by pulse generator 1100 and provided to extension lead 1110 via a plurality of terminals (not shown) on the proximal end of extension lead 1110. The electrical pulses are conducted through conductors within lead body 1111 to housing 1112. Housing 1112 includes a plurality of electrical connectors (e.g., "Bal-Seal" connectors) that are adapted to connect to the terminals of lead 1120. Thereby, the pulses originating from pulse generator 1100 and conducted through the conductors of lead body 1111 are provided to stimulation lead 1120. The pulses are then conducted through the conductors of lead 1120 and applied to tissue of a patient via electrodes 600.

In practice, stimulation lead 1120 is implanted within a suitable location within a patient adjacent to tissue of a patient to treat the patient's particular disorder(s). The lead body extends away from the implant site and is, eventually, tunneled underneath the skin to a secondary location. Housing 1112 of extension lead 1110 is coupled to the terminals of lead 1120 at the secondary location and is implanted at that secondary location. Lead body 1111 of extension lead 1110 is tunneled to a third location for connection with pulse generator 1100 (which is implanted at the third location).

Controller device 1160 may be implemented to recharge battery 1103 of pulse generator 1100 (although a separate recharging device could alternatively be employed). A "wand" 1165 may be electrically connected to controller device through suitable electrical connectors (not shown). The electrical connectors are electrically connected to coil 1166 (the "primary" coil) at the distal end of wand 1165 through respective wires (not shown). Typically, coil 1166 is connected to the wires through capacitors (not shown). Also, in some embodiments, wand 1165 may comprise one or more temperature sensors for use during charging operations.

The patient then places the primary coil 1166 against the patient's body immediately above the secondary coil (not shown), i.e., the coil of the implantable medical device. Preferably, the primary coil 1166 and the secondary coil are aligned in a coaxial manner by the patient for efficiency of the coupling between the primary and secondary cons. Controller 1160 generates an AC-signal to drive current through coil 1166 of wand 1165. Assuming that primary coil 1166 and secondary coil are suitably positioned relative to each other, the secondary coil is disposed within the field generated by the current driven through primary coil 1166. Current is then induced in secondary coil. The current induced in the coil of the implantable pulse generator is rectified and regulated to recharge battery 1103 by charging circuitry 1104. Charging circuitry 1104 may also communicate status messages to controller 1160 during charging operations using pulse-loading or any other suitable technique. For example, controller 1160 may communicate the coupling status, charging status, charge completion status, etc.

External controller device 1160 is also a device that permits the operations of pulse generator 1100 to be controlled by user after pulse generator 1100 is implanted within a patient, although in alternative embodiments separate devices are employed for charging and programming. Also, multiple controller devices may be provided for different types of users (e.g., the patient or a clinician). Controller device 1160 can be implemented by utilizing a suitable handheld processor-based system that possesses wireless communication capabilities. Software is typically stored in memory of controller device 1160 to control the various operations of controller device 1160. Also, the wireless communication functionality of controller device 1160 can be integrated within the handheld device package or provided as a separate attachable device. The interface functionality of controller device 1160 is implemented using suitable software code for interacting with the user and using the wireless communication capabilities to conduct communications with IPG 1100.

Controller device 1160 preferably provides one or more user interfaces to allow the user to operate pulse generator 1100 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 1100 modifies its internal parameters in response to the control signals from controller device 1160 to vary the stimulation characteristics of stimulation pulses transmitted through stimulation lead 1120 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating a stimulation lead for applying electrical pulses to tissue of a patient, the method comprising:
   supplying a lead body, wherein the lead body comprises a plurality of wire conductors extending from a proximal end of the lead body to a distal end of the lead body, and the plurality of wire conductors are disposed within insulative material of the lead body; and
   providing a plurality of terminals and electrodes on the proximal end and the distal end of the lead body respectively, wherein the plurality of terminals and electrodes are electrically coupled through the plurality of wire conductors;

wherein the providing comprises:
  positioning a conductive band about the lead body, wherein the conductive band comprises a first end and a second end, and the first end and the second end are adapted to be clasped together;
  positioning a wire conductor between an exterior surface of the first end and an interior surface of the second end of the conductive band;
  closing the first end and the second end of the conductive band about the wire conductor such that the first end and the second end are disposed in an overlapping arrangement; and
  welding the conductive band to sea the conductive band about the lead body.

2. The method of claim 1 wherein the exterior surface of the first end and the interior surface of the second end comprise complementary surface textures to mate the first and second ends together.

3. The method of claim 2 further comprising;
  laser etching the exterior surface of the first end and the interior surface of the second end to form the complementary surface textures.

4. The method of claim 2 further comprising:
  milling the exterior surface of the first end and the interior surface of the second end to form the complementary surface textures.

5. The method of claim 2 wherein the exterior surface of the first end and the interior surface of the second end comprise saw-tooth patterned surfaces.

6. The method of claim 2 wherein the first end and the second end comprise surface features such that when the first end and the second end are clasped together, the first end and the second end form a recess to hold the conductor wire.

7. The method of claim 1 wherein the conductive band possesses a spring characteristic to provide a biasing force to press the first end against the second end when the first end and the second end are placed in an overlapping arrangement.

8. The method of claim 1 wherein the conductive band is fabricated from a platinum iridium alloy.

9. The method of claim 1 wherein the providing further comprising:
  removing insulative material from the lead body to expose the wire conductor; and
  freeing a portion of the wire conductor to be positioned within the first end and the second end of the conductive band.

10. The method of claim 1 wherein the providing further comprising:
  removing insulative material from the lead body to expose a second conductor wire of the lead body; and
  electrically coupling the wire conductor to the exposed second conductor wire of the lead body.

11. The method of claim 1 wherein the plurality of wire conductors are helically wound within the lead body.

12. The method of claim 1 wherein the welding comprising laser welding the first end and the second end together.

13. A stimulation lead for applying electrical pulses to tissue of a patient, the stimulation lead comprising:
  a lead body comprising a plurality of wire conductors extending from a proximal end of the lead body to a distal end of the lead body, wherein the plurality of wire conductors are disposed within insulative material of the lead body; and
  a plurality of terminals and electrodes on the proximal end and the distal end of the lead body respectively, wherein the plurality of terminals and electrodes are electrically coupled through the plurality of wire conductors;
  wherein at least one of the plurality of terminals and electrodes comprises:
    a conductive band disposed about the lead body, wherein the conductive band comprises a first end and a second end, the first end and the second end are disposed in an overlapping arrangement and the first end and the second end are welded together, and a wire conductor is disposed between an exterior surface of the first end and an interior surface of the second end of the conductive band.

14. The stimulation lead of claim 13 wherein the exterior surface of the first end and the interior surface of the second end comprise complementary surface textures to mate the first and second ends together.

15. The stimulation lead of claim 14 wherein the exterior surface of the first end and the interior surface of the second end comprise saw-tooth patterned surfaces.

16. The stimulation lead of claim 14 wherein the first end and the second end comprise surface features such that when the first end and the second end are clasped together, the first end and the second end form a recess to hold the wire conductor.

17. The stimulation lead of claim 4 wherein the conductive band is fabricated from a platinum iridium alloy.

18. The stimulation lead of claim 14 wherein a distal end of the wire conductor is disposed within the conductive band and a proximal portion of the wire conductor is embedded within insulative material of the lead body.

19. The stimulation lead of claim 14 wherein the conductor wire within the conductive band is electrically coupled to a portion of a second conductor wire of the lead body exposed through insulative material of the lead body.

* * * * *

UNITED STATES PATENT AND TRADEMARK OFFICE
CERTIFICATE OF CORRECTION

Page 1 of 1

PATENT NO.         : 8,275,465 B2
APPLICATION NO.    : 12/980862
DATED              : September 25, 2012
INVENTOR(S)        : Cory Brinkman It is certified that error appears in the above-identified patent and that said Letters Patent is hereby corrected as shown below:

Column 9, claim 1, line 13, "sea" to read as --seal--

Column 9, claim 3, end of line 19, ";" to read as --:--

Column 10, claim 17, line 42, "4" to read as --14--

Signed and Sealed this
Twenty-seventh Day of November, 2012

David J. Kappos
*Director of the United States Patent and Trademark Office*